United States Patent
Weldon et al.

(10) Patent No.: US 11,590,165 B2
(45) Date of Patent: Feb. 28, 2023

(54) FORMULATIONS OF CALCIUM AND PHOSPHATE FOR ORAL INFLAMMATION

(71) Applicant: Bausch Health Companies Inc., Laval (CA)

(72) Inventors: Bartholomew Weldon, Chicago, IL (US); Edward Kobus, Franklin Lakes, NJ (US); Sandryne Dumoulin, Laval (CA); Aimesther Betancourt, Laval (CA); Patrick Gosselin, Laval (CA)

(73) Assignee: BAUSCH HEALTH COMPANIES INC., Laval (CA)

( * ) Notice: Subject to any disclaimer, the term of this patent is extended or adjusted under 35 U.S.C. 154(b) by 567 days.

(21) Appl. No.: 14/945,865

(22) Filed: Nov. 19, 2015

(65) Prior Publication Data
US 2016/0175356 A1 Jun. 23, 2016

Related U.S. Application Data

(60) Provisional application No. 62/093,026, filed on Dec. 17, 2014.

(51) Int. Cl.
| | |
|---|---|
| *A61K 33/42* | (2006.01) |
| *A61K 33/14* | (2006.01) |
| *A61K 33/00* | (2006.01) |
| *A61K 31/191* | (2006.01) |
| *A61K 9/00* | (2006.01) |
| *A61K 9/14* | (2006.01) |
| *A61P 1/02* | (2006.01) |
| *A61K 31/19* | (2006.01) |
| *A61K 31/661* | (2006.01) |
| *A61K 45/06* | (2006.01) |
| *A61K 47/02* | (2006.01) |

(52) U.S. Cl.
CPC ........... *A61K 33/42* (2013.01); *A61K 9/006* (2013.01); *A61K 9/0053* (2013.01); *A61K 9/0095* (2013.01); *A61K 9/143* (2013.01); *A61K 31/19* (2013.01); *A61K 31/191* (2013.01); *A61K 31/661* (2013.01); *A61K 33/00* (2013.01); *A61K 33/14* (2013.01); *A61K 45/06* (2013.01); *A61K 47/02* (2013.01); *A61P 1/02* (2018.01)

(58) Field of Classification Search
CPC ...... A61K 33/42; A61K 9/0053; A61K 9/006; A61K 9/0095; A61K 9/143; A61K 31/19; A61K 31/191; A61K 31/661; A61K 33/00; A61K 33/14; A61K 45/06; A61K 47/02; A61P 1/02
See application file for complete search history.

(56) References Cited

U.S. PATENT DOCUMENTS

| | | | |
|---|---|---|---|
| 4,716,035 A | 12/1987 | Kumar | |
| 5,268,267 A | 12/1993 | Smith | |
| 5,427,768 A | 6/1995 | Tung | |
| 5,540,913 A | 7/1996 | Turner | |
| 5,993,785 A | 11/1999 | Johansen et al. | |
| 6,387,352 B1 | 5/2002 | Johansen et al. | |
| 6,645,988 B2 * | 11/2003 | Phillips | A61K 9/0007 514/338 |
| 8,247,440 B2 * | 8/2012 | Phillips | A61K 9/2009 514/395 |
| 8,518,383 B2 | 8/2013 | Haas | |
| 8,597,691 B2 * | 12/2013 | Satou | A61K 33/00 424/717 |
| 2003/0152530 A1 * | 8/2003 | Johansen | A61K 8/24 424/57 |
| 2003/0191159 A1 * | 10/2003 | Phillips | A61K 9/0007 514/338 |
| 2004/0248942 A1 * | 12/2004 | Hepburn | A61K 45/06 514/338 |
| 2005/0054682 A1 * | 3/2005 | Phillips | A61K 9/0007 514/338 |
| 2005/0112193 A1 * | 5/2005 | Phillips | A61K 9/5026 424/464 |
| 2005/0249806 A1 * | 11/2005 | Proehl | A61K 45/06 424/464 |
| 2006/0159632 A1 | 7/2006 | Ishibashi et al. | |
| 2007/0166407 A1 * | 7/2007 | Tanaka | A61K 31/765 424/727 |

(Continued)

FOREIGN PATENT DOCUMENTS

| | | |
|---|---|---|
| CN | 1192672 A | 9/1998 |
| CN | 101584889 A | 11/2009 |

(Continued)

OTHER PUBLICATIONS

Gerstner. Calcium Lactate Gluconate—The Innovative Solution for Extra Calcium. Innovation in Food Technology 2002, 16:1-3.*

(Continued)

*Primary Examiner* — Robert A Wax
*Assistant Examiner* — Olga V. Tcherkasskaya
(74) *Attorney, Agent, or Firm* — Andrew J. Anderson, Esq.; Harter Secrest & Emery LLP

(57) ABSTRACT

The present invention generally relates to liquid compositions and methods for treating oral inflammation by administering a liquid composition to the oral cavity. The liquid composition is prepared from a powder containing calcium glycerophosphate, one or more sodium phosphate salts, sodium chloride, and optionally sodium bicarbonate and silica. The powder is mixed with a quality of water to form a liquid that is supersaturated with calcium ions and phosphate ions and is essentially free of visible particles and precipitate.

10 Claims, No Drawings

(56) References Cited

U.S. PATENT DOCUMENTS

| | | | |
|---|---|---|---|
| 2007/0185194 A1* | 8/2007 | Mehta | A61K 9/0095 514/460 |
| 2007/0237725 A1* | 10/2007 | Tancredi | A23G 3/362 424/48 |
| 2009/0023771 A1* | 1/2009 | Phillips | A61K 31/44 514/303 |
| 2009/0130232 A1 | 5/2009 | Zahra | |
| 2009/0239957 A1* | 9/2009 | Shah | A61K 47/02 514/770 |
| 2010/0158819 A1* | 6/2010 | Kligerman | A61K 9/0043 424/45 |
| 2011/0086108 A1 | 4/2011 | Weldon | |
| 2012/0034280 A1* | 2/2012 | Cohen | A61K 8/20 424/401 |
| 2012/0289550 A1* | 11/2012 | Phillips | A61K 9/2009 514/338 |
| 2015/0272873 A1* | 10/2015 | Boschetti | A61K 8/24 424/44 |

FOREIGN PATENT DOCUMENTS

| | | |
|---|---|---|
| JP | 2009235012 A | 10/2009 |
| JP | 2011126802 A | 6/2011 |
| WO | 97006774 A | 2/1997 |
| WO | 2010/054494 A2 | 5/2010 |

OTHER PUBLICATIONS

International Search Report and Written Opinion of the International Searching Authority received in corresponding International Application No. PCT/CA2015/051327, completed Feb. 18, 2016 (10 pages).

Corral, LG et al.: "Antimicrobial activity of sodium bicarbonate"—J Food Science (1988) 53; 3: 981-982.

Carl & Emrich: "Management of oral mucositis during local radiation and systemic chemotherapy: A study of 98 patients"—J Prosthet Dent (1991), 66: 361-69.

Papas AS et al.: "A prospective, randomized trial for the prevention of mucositis in patients undergoing hematopoietic stem cell transplantation"—Bone Marrow Transplantation (2003), 31: 705-12.

Levin: "The Beneficial Effects of a Supersaturated Calcium Phosphate Rinse on the Oral Cavity in Xerostomia Patients" Dental CE Digest (May 2014), pp. 1-7, INeedCE.com, Supplement to PennWell Publications.

* cited by examiner

FORMULATIONS OF CALCIUM AND PHOSPHATE FOR ORAL INFLAMMATION

FIELD OF THE INVENTION

The present invention involves the formulation of powders which, when dissolved in water, form a liquid composition supersaturated with calcium and phosphate ions. The liquid composition can be used as an oral rinse for the prevention and treatment of inflammation of the soft tissues of the oral cavity, which may result from infection or trauma to the oral mucosal tissue, or for the prevention or treatment of xerostomia or chronic hyposalivation or complications therefrom.

BACKGROUND OF THE INVENTION

Human saliva plays a number of roles in the oral cavity, including aiding in the prevention and healing of infections in the mouth and the remineralization of teeth. Saliva is made up of many inorganic and organic components, including electrolytes, proteins, immunoglobulins, enzymes, mucins, urea, and ammonia. The inorganic components include sodium bicarbonate, which aids in the buffering capacity of saliva. Saliva also includes calcium and phosphate ions in supersaturated states which allow for the maintenance of tooth mineral integrity and promotion of soft tissue healing. It is believed that calcium plays a role in preventing oral infection, protecting the oral mucosa and healing wounds in the mouth. Phosphate helps to modulate pH balance in the mouth, protecting the teeth and repairing mucosal damage.

A commercially available powder product manufactured by Invado Pharmaceutical, LLC and sold under the trademark NeutraSal® is indicated for the dryness of the mouth (hyposalivation, xerostomia); dryness of the oral mucosa due to drugs such as antihistamines or atropine or other anticholinergic agents that suppress salivary secretion; and as part of an oral hygiene program for patients with dry mouth. Relief of dryness of the oral mucosa in these conditions is associated with amelioration of pain. The NeutraSal® product that has been provided commercially is a powder containing about calcium chloride dihydrate, sodium chloride, sodium phosphate salts, and sodium bicarbonate. The commercial product is provided in packets containing 538 mg of powder, and the directions state that the powder should be mixed in 30 ml of tap, distilled or purified water, thereby forming a liquid that is supersaturated with both calcium and phosphate ions. The NeutraSal® powder contains a theoretical concentration of calcium ions between 20,000 ppm and 25,000 ppm and a theoretical concentration of phosphate ions (as phosphate) between 45,000 ppm and 60,000 ppm (calculated based on the weight percentage of each component of the dry power).

A commercially available product from Jazz Pharmaceuticals that provides an electrolyte solution as a mouth rinse to moisten, lubricate and clean the oral cavity including the mucosa of the mouth, tongue and throat is sold under the trademark Caphosol®. Caphosol® is said to contain dibasic sodium phosphate 0.032% w/w, monobasic sodium phosphate 0.009% w/w, calcium chloride 0.052% w/w, sodium chloride 0.569% w/w, and purified water qs ad. Caphosol® is not provided as a powder; instead it is provided in two separately packaged aqueous solutions, a phosphate solution (Caphosol® A) and a calcium solution (Caphosol® B) which, when both ampule solutions are combined in equal volumes, form a solution supersaturated with respect to both calcium and phosphate ions.

Additional information regarding oral rinses may be found in Tung U.S. Pat. No. 5,268,267; Tung U.S. Pat. No. 5,427,768; Johansen et al. U.S. Pat. No. 5,993,785; Johansen et al. U.S. Pat. No. 6,387,352; Zahra et al. US Pat. Publication No. 20090130232; Ishibashi et al. US Pat. Publication No. 20060159632, Sampathkumar U.S. Pat. No. 4,716,035, Turner U.S. Pat. No. 5,540,913; Papas A S et al, "A prospective, randomized trial for the prevention of mucositis in patients undergoing hematopoietic stem cell transplantation", Bone Marrow Transplantation (2003), 31: 705-12; Carl & Emrich, "Management of oral mucositis during local radiation and systemic chemotherapy: A study of 98 patients", J Prosthet Dent (1991), 66: 361-69; Corral, L G et al, "Antimicrobial activity of sodium bicarbonate" J Food Science (1988) 53; 3: 981-982.

Weldon US Publication No. 2011/0086108 was assigned to the original assignee as the present invention (Invado Pharmaceuticals LLC). It discloses stable powders which, when dissolved in water, form a non-pressurized carbonated solution supersaturated with calcium and phosphate ions, and also containing the presence of carbon dioxide and sodium bicarbonate. The resulting solution can be used as an oral rinse for the prevention and treatment of inflammatory processes of the soft tissues of the mouth, throat and oral cavity, which may result from infection or trauma to the oral mucosal tissue.

Levin, "The Beneficial Effects of a Supersaturated Calcium Phosphate Rinse on the Oral Cavity in Xerostomia Patients" (May 2014), discusses the beneficial effects of supersaturated calcium phosphate rinse for the xerostomia patient. Both calcium phosphate and sodium bicarbonate ions found in supersaturated calcium phosphate rinse play significant roles in healing and protecting tissues of the oral cavity. Supersaturated calcium phosphate rinse is not a cure for xerostomia, but it is a powerful adjuncts in the care and treatment of the wide variety of symptoms and severities of dry mouth associated with xerostomia patients.

SUMMARY OF THE INVENTION

The present invention provides a composition useful for treating oral injury, oral inflammation, or oral pain. The present invention employs comprises calcium glycerophosphate, calcium lactate gluconate, or a mixture thereof.

As one aspect of the present invention, a powder is adapted for producing a liquid composition for treating oral injury, oral inflammation and/or oral pain. The powder comprises calcium glycerophosphate or calcium lactate gluconate; a sodium phosphate; and sodium chloride. For example, the powder can comprise calcium glycerophosphate in an amount at least about 5% w/w and at most 25% w/w of the powder, and/or the powder can comprise dibasic sodium phosphate anhydrous, present in an amount at least about 0.5% w/w and at most about 10% w/w of the powder, and/or monobasic sodium phosphate anhydrous, present in an amount at least about 0.3% w/w and at most about 6% w/w of the powder. In some embodiments, powder comprises at least 20,000 ppm calcium ions; at least 60,000 ppm phosphate ions, calculated based on weight percentages of solid components in the powder. In some embodiments, the powder comprises a pH buffering agent such as sodium bicarbonate, a liquid composition prepared from the powder has a pH between about 6.5 and about 7.5.

As another aspect of the present invention, a method is provided for treating a subject having an oral cavity. The method comprises mixing a powder as described herein with water to form a liquid composition; admitting the liquid composition into the oral cavity of the subject, wherein the subject is in need of treatment for one or more of oral injury, oral inflammation, or oral pain; moving the composition within the oral cavity; and expelling the composition from the oral cavity of the subject.

As another aspect of the present invention, a liquid composition is provided for use in preventing or treating oral injury, oral inflammation and/or oral pain. The liquid composition can also be used for preventing or treating xerostomia or chronic hyposalivation or complications from hyposalivation. The liquid composition is supersaturated in calcium ions and phosphate ions. In some embodiments, the liquid composition is essentially free of visible particles or precipitates. In some embodiments, the liquid composition is the product of mixing a powder as described herein, in a weight ratio of powder to water include from about 0.005:1 about 0.1:1.

DETAILED DESCRIPTION

The present disclosure is based in part on a desire for a product that is easy to manufacture, store, and use in the treatment of oral injury, oral inflammation, and/or relief of pain in the oral cavity. Liquid compositions are provided for treating oral injury, oral inflammation and/or oral pain by administering such compositions to a subject in need of treatment. It is known that human saliva is normally supersaturated with respect to calcium and phosphate. The oral rinse created by the powders contain significantly higher concentrations of calcium and phosphate ions than normally found in saliva. The resulting liquid composition may be supersaturated with calcium and phosphate ions in the order of 10, 100 or more times those found in normal human saliva.

In some embodiments, the present invention can be provided as a powder containing a mixture of calcium glycerophosphate or calcium lactate gluconate, monobasic and dibasic phosphate salts, one or more pH buffering agents, particularly sodium bicarbonate, sodium chloride and optionally xylitol. The powder can also contain silica and/or other components. When a suitable amount of water is added to such powders, for example, in a powder to water weight ratio of about 0.018 to about 1, the powder will dissolve rapidly to create a liquid composition supersaturated with respect to calcium and phosphate ions and having a pH in the range of about 6.5 to about 7.5, alternatively between about 7 and about 7.4. The present invention can also be provided as the liquid composition prepared from such a powder.

The present liquid compositions or powders can also comprise solutes found naturally occurring in saliva, analgesics, flavoring, preservatives, a fluoride salt or fluoride ions, a strontium salt or strontium ions, and/or a hydrophilic polymer. The present liquid compositions or powders can also comprise one or more preservatives, analgesics, antihistamines, corticosteroids, anti-microbial agents, and/or anti-fungal agents. The components of the powder are preferably food-grade ingredients.

In some embodiments, calcium glycerophosphate or calcium lactate gluconate or a mixture thereof is at least about 5% w/w, alternatively at least about 6% w/w, alternatively at least about 7% w/w, alternatively at least about 8% w/w, alternatively at least about 9% w/w, alternatively at least about 10% w/w, alternatively at least about 11% w/w, alternatively at least about 12% w/w, alternatively at least about 13% w/w, alternatively at least about 14% w/w, alternatively at least about 15% w/w, of the powder. In some embodiments, the calcium glycerophosphate or calcium lactate gluconate or a mixture thereof is at most about 25% w/w, alternatively at most about 24% w/w, alternatively at most about 23% w/w, alternatively at most about 22% w/w, alternatively at most about 21% w/w, alternatively at most about 20% w/w, alternatively at most about 19% w/w, alternatively at most about 18% w/w, alternatively at most about 17% w/w, alternatively at most about 16% w/w, alternatively at most about 15% w/w, of the powder. The foregoing maxima and minima may be combined to form a range, so long as the minimum is less than the maximum.

In some embodiments, calcium glycerophosphate or calcium lactate gluconate is present in the powder in an amount corresponding to a calcium ion concentration of at least 1,000 ppm, alternatively at least 2,000 ppm, alternatively at least 5,000 ppm, alternatively at least 10,000 ppm, alternatively at least 15,000 ppm, alternatively at least 20,000 ppm, alternatively at least or at most 22,000 ppm, alternatively at least or at most 25,000 ppm, alternatively at least or at most 30,000 ppm, alternatively at most 40,000 ppm. The calcium ion concentration is calculated based on weight percentages of solid components in the powder. The foregoing maxima and minima may be combined to form a range, so long as the minimum is less than the maximum.

Suitable phosphate salts may include sodium phosphates (such as dibasic sodium phosphate anhydrous and monobasic sodium phosphate anhydrous), potassium phosphates, potassium citrate, and others. In some embodiments, the phosphate salt(s) is present in the powder in an amount corresponding to a phosphate ion concentration of at least 5,000 ppm, alternatively at least 10,000 ppm, alternatively at least 20,000 ppm, alternatively at least 50,000 ppm, alternatively at least 60,000 ppm, alternatively at least or at most 65,000 ppm, alternatively at least or at most 70,000 ppm, alternatively at least or at most 75,000 ppm, alternatively at least or at most 80,000 ppm, alternatively at most 90,000 ppm. The phosphate ion concentration is calculated based on weight percentages of solid components in the powder. The foregoing maxima and minima may be combined to form a range, so long as the minimum is less than the maximum.

In some embodiments, dibasic sodium phosphate anhydrous is at least about 0.5% w/w, alternatively at least about 0.7% w/w, alternatively at least about 1% w/w, alternatively at least about 1.1% w/w, alternatively at least about 1.2% w/w, alternatively at least about 2% w/w, alternatively at least about 2.5% w/w, alternatively at least about 4% w/w, of the powder. In some embodiments, dibasic sodium phosphate anhydrous is at most about 10% w/w, alternatively at most about 7.5% w/w, alternatively at most about 6% w/w, alternatively at most about 5% w/w, alternatively at most about 4% w/w, alternatively at most about 3.25% w/w, alternatively at most about 3% w/w, alternatively at most about 2.5% w/w, alternatively at most about 2% w/w, alternatively at most about 1.5% w/w, of the powder. The foregoing maxima and minima may be combined to form a range, so long as the minimum is less than the maximum.

In some embodiments, monobasic sodium phosphate anhydrous is at least about 0.3% w/w, alternatively at least about 0.5% w/w, alternatively at least about 0.6% w/w, alternatively at least about 0.7% w/w, alternatively at least about 0.8% w/w, alternatively at least about 0.9% w/w, alternatively at least about 1% w/w, alternatively at least about 1.5% w/w, alternatively at least about 2% w/w, alternatively at least about 2.5% w/w, alternatively at least about 3% w/w, of the powder. In some embodiments, monobasic sodium phosphate anhydrous is at most about 6% w/w, alternatively at most about 5% w/w, alternatively at most about 4% w/w, alternatively at most about 3.5% w/w, alternatively at most about 3% w/w, alternatively at most about 2.5% w/w, alternatively at most about 2% w/w, alternatively at most about 1.5% w/w, alternatively at most about 1% w/w, alternatively at most about 0.9% w/w, alternatively at most about 0.85% w/w, of the powder. The foregoing maxima and minima may be combined to form a range, so long as the minimum is less than the maximum.

In some embodiments, sodium bicarbonate or another pH buffering agent is included in the powder. The pH buffering agent (preferably sodium bicarbonate) can be at least about 1% w/w, alternatively at least about 1.5% w/w, alternatively at least about 2% w/w, alternatively at least about 2.5% w/w, alternatively at least about 3% w/w, alternatively at least about 3.5% w/w, alternatively at least about 4% w/w, alternatively at least about 4.5% w/w, alternatively at least about 5% w/w, alternatively at least about 5.5% w/w, alternatively at least about 6% w/w, of the powder. In some embodiments, sodium bicarbonate can be at most about 9% w/w, alternatively at most about 8.5% w/w, alternatively at most about 8% w/w, alternatively at most about 7.5% w/w, alternatively at most about 7% w/w, alternatively at most about 6.5% w/w, alternatively at most about 6% w/w, alternatively at most about 5.5% w/w, alternatively at most about 5% w/w, alternatively at most about 4.9% w/w, alternatively at most about 4.5% w/w, of the powder. The foregoing maxima and minima may be combined to form a range, so long as the minimum is less than the maximum.

Suitable analgesics include benzocaine, lidocaine, tetracaine, hexylcaine, bupivacaine, proparacaine, prilocaine, benoxinate, mepivacaine, propoxycaine, dyclonine, pramoxine, mepivacaine, procaine, chloroprocaine, ropivacaine, dibucaine, and etidocaine, and mixtures thereof.

Suitable preservatives include food-grade preservatives or preservative systems, such as sorbic acid and its salts, benzoic acid and its salts, calcium propionate, sodium nitrite, sodium nitrate, sulfites (such as sulfur dioxide, sodium bisulfite, and potassium hydrogen sulfite) disodium EDTA, butylated hydroxyanisole (BHA), butylated hydroxytoluene (BHT), tert-butyl hydroquinone (TBHQ), and propyl gallate.

Suitable antihistamines include diphenhydramine, which can provide anti-inflammatory benefits. Suitable corticosteroids include prednisone. Diphenhydramine and/or prednisone are contemplated as preferred ingredients for providing anti-inflammatory benefits.

Suitable anti-microbial agents include chlorhexidine and peroxide compounds. Suitable anti-fungal agents include nystatin and amphotericin.

Suitable food-grade hydrophilic polymers may include polyalkylene glycols such as polyethylene glycols, carbomers or other polymers of acrylic acid, and gums such as guar gum. The present compositions can include from 0.1% to 70% by weight, alternatively from 0.5% to 25% by weight, alternatively from 1% to 20% by weight, alternatively from 5% to 15% by weight, of the hydrophilic polymer, based on the total weight of the powder.

The present disclosure also provides methods of preparing liquid compositions suitable for use in the treatment of oral injury, oral inflammation and/or oral pain. Suitable compositions are prepared as follows. A powder is combined and mixed with an appropriate volume of water to achieve the consistency desired. For example, 538 mg of powder (or another amount) can be mixed with 30 ml (30 g) or 40 ml (40 g) or another suitable amount of water. Preferred weight ratios of powder to water include from about 0.005:1 about 0.1:1, alternatively 0.01:1 to about 0.05:1, alternatively about 0.015:1 to about 0.02:1. The present disclosure provides liquid compositions that are essentially free of visible particles or precipitates at the foregoing weight ratios of powder to water. The water can be distilled water, tap water, bottled water or water from another source. The powder can be packaged in a packet such as a tube, sachet, or other container. The packet can be essentially moisture impermeable, such as a foil packet.

The present disclosure also provides methods for treating oral wounds, oral mucotitis or inflammation, oral pain, xerostomia, chronic hyposalivation or complications therefrom. The methods comprise administering a liquid composition as described herein, for example, as a liquid oral rinse, to a subject in need of treatment. In some embodiments, the oral inflammation, injury or pain arises from an infection to the mouth, including but not limited to candidiasis, moniliasis, reactivation of latent virus and secondary infections, septicaemia, and combinations thereof. In some embodiments, the inflammation is part of the broader syndrome associated with oral mucositis, erythema, Sjogren's Syndrome and any combination thereof. The present methods can also be used for treatment of oral inflammation associated with immune-compromised patients including bone marrow transplant patients and AIDS patients, or associated with chemotherapy or radiation treatment.

In some embodiments, the present disclosure provides methods for treating xerostomia and/or chronic hyposalivation that arise as a medication side effect, dehydration, radiotherapy involving the salivary glands, or a disease. Medications with xerogenic side effects include antihistamines, antidepressants, anticholenergics, anorexiants, antihypertensives, antipsychotics, anti-Parkinson agents, diuretics and sedatives. Diseases that cause xerostomia include Sjogren's Syndrome, rheumatoid arthritis, systemic lupus erythematosus, scleroderma, diabetes mellitus, hypertension, cystic fibrosis, and diseases of the salivary gland. Complications of xerostomia and/or chronic hyposalivation include tooth decay, dental caries, oral candidiasis, dysgeusia, oral dysesthesia, and others. The present methods can be used for the prevention and treatment of dysphagia and/or stomatitis. The methods comprise administering a liquid composition as described herein, for example, as a liquid oral rinse, to a subject in need of treatment.

Salivary pH in a subject suffering from xerostomia is commonly acidic, having a pH of 6.4 or less. *S. mutans* bacteria thrive in an acidic environment. In xerostomic patients it is not uncommon to see elevated levels of *S. mutans* bacteria, often exceeding 500,000 colony-forming units (CFU). Elevated levels of *S. mutans* increase the risk for dental caries. Buffering the salivary pH can modulate and/or reduce the levels of *S. mutans* to lower levels (such as less than 500,000 CFU). Buffering the salivary pH also allows for less erosive tissue lesions. Accordingly, in some embodiments, the present disclosure provides methods for modulating the average salivary pH in the oral cavity of a subject in need of such modulation, such as a subject suffering from xerostomia and/or chronic hyposalivation, by administering a liquid composition as described herein to such a subject. In some embodiments, the average salivary pH is raised at least 0.3 pH units, alternatively at least 0.5 pH units, alternatively at least 0.7 pH units, alternatively at least 1 pH unit, alternatively at least 1.2 pH unit. In some embodiments, the average salivary pH is raised to at least 6, alternatively at least 6.2, alternatively at least 6.5, alternatively at least 6.6, alternatively at least 6.7, alternatively at least 6.8, alternatively at least 6.9, alternatively at least 7, alternatively at least 7.1. In some embodiments, the present disclosure provides methods for balancing or reducing microflora, such as *S. mutans* bacteria, by administering a liquid composition as described herein to a subject in need of treatment. For example, the *S. mutans* population in the oral cavity of a subject can be reduced from greater than 500,000 cfu/ml to less than 500,000 cfu/ml, alternatively less than 350,000 cfu/ml, alternatively less than 200,000 cfu/ml.

The liquid compositions are designed to be physiologically compatible with both intact and compromised tissue in the mouth, and will alleviate pain associated with all types of injury to the mucosal tissue of the mouth and oral cavity. The pH and osmotic pressure of the compositions can be adjusted to be compatible with saliva, such as by including an appropriate amount of sodium bicarbonate, for example. Sodium bicarbonate assists in balancing the pH and buffering of oral acids in the mouth.

In some embodiments, the present methods comprise admitting a liquid composition into a mouth of a subject in need of treatment, swirling or gargling the liquid composition, and expelling the liquid composition from the subject's mouth.

The pH and osmotic pressure of the liquid composition can be adjusted to be compatible with saliva. Suitable pH ranges for the liquid composition comprise from 5.5 to 7.8, alternatively from 6 to 7.5, alternatively from 6.6 to 7.1, alternatively from 6.8 to 7.

EXAMPLES

Example 1

This example describes testing done to explore cause(s) of the formation of visible particles or precipitates that were seen at times in supersaturated oral rinses. Table 1 provides a description of the visual solubility tests performed using various components (including a commercial sample), with the quantities of each product weighed, and visual observations after the components were mixed in water. The tests were undertaken out of a desire to evaluate the cause of visible particles or precipitates that were seen, as avoiding the particles or precipitates could provide a more visually pleasing product though they do not cause any problems with the efficacy of the product.

To evaluate dissolution, the components were weighed and put in centrifuge tubes containing 30 ml of tap water at room temperature. The tubes were gently stirred by hand (up and down movements) for 30 seconds to 1 minute. The dispersions were then assessed visually for turbidity and presence of particles in suspension or precipitate. pH was also assessed using pH meter Mettler Toledo Seven Multi and following USP <791> method.

Only two samples yielded particles in suspension or precipitates: the commercial sample (Test 12) and the combination of dibasic sodium phosphate anhydrous and calcium chloride dihydrate (Test 7). Thus, the testing demonstrated the relative insolubility of dibasic sodium phosphate anhydrous and calcium chloride dihydrate when combined at those concentrations. Also, a slightly opaque liquid was observed when using sodium chloride from one source (Test 4) but a transparent solution was observed with sodium chloride reagent sourced from another supplier (Test 13).

TABLE 1

| Test | Ingredient 1 | Ingredient 2 | Weight of ingredient 1 (mg) | Weight of ingredient 2 (mg) | Visual Observations | pH |
|---|---|---|---|---|---|---|
| 1 | Dibasic Sodium Phosphate anhydrous | NA | 28.4 | NA | Dissolved (1 min) | NA |
| 2 | Monobasic Sodium Phosphate | NA | 17.2 | NA | Dissolved (30 sec) | NA |
| 3 | Calcium Chloride dihydrate | NA | 44.1 | NA | Dissolved (30 sec) | NA |
| 4 | Sodium Chloride | NA | 404.9 | NA | Dissolved (slightly opaque) | NA |
| 5 | Sodium Bicarbonate | NA | 44.6 | NA | Dissolved (30 sec) | NA |
| 6 | Silica | NA | 2.1 | NA | Dissolved (30 sec) | NA |
| 7 | Dibasic Sodium Phosphate anhydrous | Calcium Chloride dihydrate | 27.4 | 44.0 | Not dissolved | 5.96 |
| 8 | Monobasic Sodium Phosphate | Calcium Chloride dihydrate | 17.5 | 44.0 | Dissolved (30 sec) | 5.78 |
| 9 | Calcium Chloride dihydrate | Sodium Chloride | 44.1 | 404.6 | Dissolved (slightly opaque) | NA |
| 10 | Calcium Chloride dihydrate | Sodium Bicarbonate | 44.6 | 44.5 | Dissolved (30 sec) | NA |
| 11 | Calcium Chloride dihydrate | Silica | 44.5 | 3.1 | Dissolved (30 sec) | NA |
| 12 | Commercial Sample | NA | 543.8 | NA | Not dissolved | 6.34 |
| 13 | Sodium chloride reagent | NA | 404.9 | NA | Dissolved (30 sec) | NA |
| 14 | Dibasic Sodium Phosphate anhydrous | Monobasic Sodium Phosphate | 29.4 | 19.7 | Dissolved (1 min) | NA |
| 15 | Dibasic Sodium Phosphate anhydrous | Sodium Chloride | 25.8 | 408.3 | Dissolved (slightly opaque) | NA |

TABLE 1-continued

| Test | Ingredient 1 | Ingredient 2 | Weight of ingredient 1 (mg) | Weight of ingredient 2 (mg) | Visual Observations | pH |
|---|---|---|---|---|---|---|
| 16 | Dibasic Sodium Phosphate anhydrous | Sodium Bicarbonate | 27.0 | 46.5 | Dissolved (1 min) | NA |
| 17 | Dibasic Sodium Phosphate anhydrous | Silica | 29.8 | 2.0 | Dissolved (1 min) | NA |
| 18 | Monobasic Sodium Phosphate | Sodium Chloride | 16.3 | 407.2 | Dissolved (slightly opaque) | NA |
| 19 | Monobasic Sodium Phosphate | Sodium Bicarbonate | 19.7 | 47.1 | Dissolved (30 sec) | NA |
| 20 | Monobasic Sodium Phosphate | Silica | 17.1 | 1.9 | Dissolved (30 sec) | NA |

These observations show that most combinations of these components dissolve within 30 seconds or 1 minute in 30 ml of room temperature tap water, but certain combinations of components at certain concentrations do not dissolve adequately.

Example 2

In order to avoid the formation or presence of visible particles and precipitates caused by the combination of dibasic sodium phosphate anhydrous and calcium chloride dihydrate, other ingredients were evaluated as potential substitutes. Visual solubility tests were done in duplicate using 3 different calcium sources. The quantity of material was adjusted in order to maintain a consistent calcium content from each different salt. Table 2 shows the solid compositions made, the visual observations when those compositions were mixed with 30 ml of tap water at room temperature, and the measured pH for the resulting liquid composition. Calcium chloride dihydrate was tested from two different sources. pH was also assessed for all dispersions. Calcium chloride from both sources, calcium glycerophosphate and calcium lactate gluconate salts were all found to be sufficiently soluble with a resulting pH of between 7.6 and 8.1. The calcium lactate gluconate salt has a lower calcium content versus other salts evaluated, so it may not be preferred for some embodiments.

TABLE 2

| | | Weight (mg) | | | pH | |
|---|---|---|---|---|---|---|
| Test | Ingredient | trial 1 | trial 2 | Observations | trial 1 | trial 2 |
| 1 | Tap water | NA | NA | NA | 7.55 | 7.44 |
| 2 | Calcium Chloride dihydrate | 44.0 | 44.1 | Dissolved (1 min)* | 7.65 | 7.67 |
| 3 | Calcium glycerophosphate | 63.1 | 63.3 | Dissolved (1 min)* | 8.08 | 8.07 |
| 4 | Calcium lactate gluconate | 133.4 | 133.3 | Dissolved (1 min)* | 7.73 | 7.74 |

*same observation for both trials

Example 3

Tables 3 to 5 provide a description of the tests performed on combinations of different calcium sources, each table describing a different mix calcium and sodium phosphate salts. It was found that both calcium salts were incompatible with dibasic sodium phosphate at those concentrations. It was also found that glycerophosphate salt led to higher pH for the liquid composition.

TABLE 3

| Item | Ingredient name | mg/unit | weighed | Solubility in 30 ml water | pH |
|---|---|---|---|---|---|
| a | Dibasic Sodium Phosphate | 27 | 27.1 | Not dissolved (slightly opaque) | 5.81 |
| b | Monobasic Sodium Phosphate | 17 | 18.3 | | |
| c | Calcium Chloride Dihydrate | 44 | 44.1 | | |

TABLE 4

| Item | Ingredient name | mg/unit | weighed | Solubility in 30 ml water | pH |
|---|---|---|---|---|---|
| a | Dibasic Sodium Phosphate | 27 | 27.5 | Not dissolved (slightly opaque) | 5.91 |
| b | Monobasic Sodium Phosphate | 17 | 18.5 | | |
| c | Calcium Chloride Dihydrate | 44 | 44.4 | | |

TABLE 5

| Item | Ingredient name | mg/unit | weighed | Solubility in 30 ml water | pH |
|---|---|---|---|---|---|
| a | Dibasic Sodium Phosphate | 27 | 27.1 | Not dissolved (slightly opaque) | 6.76 |
| b | Monobasic Sodium Phosphate | 17 | 17.9 | | |
| c | Calcium Chloride Dihydrate | 67 | 67.9 | | |

Example 4

The following trials were performed in order to assess visual solubility and pH levels of various formulations. In Examples 4a, 4b and 4c, silica was actually not included, as it does not affect pH or solubility of the other components, but its amount in prospective formulations as sown in Tables 7-9. Examples 4d and 4e contained no original ingredients from Invado and silica (colloidal silicon dioxide) was part of the blends. All lots were prepared by dry blending by hand of ingredients using spatula. Formulation details, visual solubility and pH of experiments can be found below as well as in Tables 6 to 10.

Example 4a was prepared as a reference blend with the components and percentages shown in Table 6. As expected, this formulation resulted in precipitation when mixed with 30 ml water at room temperature.

TABLE 6

| Item | Ingredient name | % | mg/unit | Solubility in 30 ml of tap water | pH |
|---|---|---|---|---|---|
| a | Dibasic Sodium Phosphate Anhydrous | 4.98% | 26.78 | opaque suspension (particles precipitation) | 6.88 |
| b | Monobasic Sodium Phosphate Anhydrous | 3.17 | 17.04 | | |
| c | Calcium Chloride Dihydrate | 8.14% | 43.82 | | |
| d | Sodium Chloride crystalline | 75.11% | 404.11 | | |
| e | Sodium Bicarbonate | 8.14% | 43.82 | | |
| f | Silica | 0.45% | 2.43 | | |
| | TOTAL | 100.00% | 538.00 | | |

Example 4b was prepared by reducing sodium chloride original quantity by 100 mg (from 404.11 mg to 304.11 mg), giving a final blend of powder of 438.0 mg instead of 538.0 mg. The components and their amounts are shown in Table 7. This formulation also yielded precipitation when mixed with 30 ml water at room temperature.

TABLE 7

| Item | Ingredient name | % | mg/unit | Solubility in 30 ml of tap water | pH |
|---|---|---|---|---|---|
| a | Dibasic Sodium Phosphate Anhydrous | 6.11% | 26.78 | opaque suspension (particles precipitation) | 6.93 |
| b | Monobasic Sodium Phosphate Anhydrous | 3.89% | 17.04 | | |
| c | Calcium Chloride Dihydrate | 10.00% | 43.82 | | |
| d | Sodium Chloride crystalline | 69.43% | 304.11 | | |
| e | Sodium Bicarbonate | 10.00% | 43.82 | | |
| f | Silica | 0.55% | 2.43 | | |
| | TOTAL | 100.00% | 438.00 | | |

Example 4c was prepared by substituting the calcium chloride dihydrate salt used in original formula by calcium glycerophosphate salt without dibasic sodium phosphate (Table 9). Without dibasic sodium phosphate, the dispersion produced was turbid but no particles in suspension and visible precipitate were observed.

TABLE 8

| Item | Ingredient name | % | mg/unit | Solubility in 30 ml of tap water | pH |
|---|---|---|---|---|---|
| a | Dibasic Sodium Phosphate Anhydrous | 0.00% | 0 | cloudy appearance | 7.02 |
| b | Monobasic Sodium Phosphate Anhydrous | 3.21% | 17.04 | | |
| c | Calcium Glycerophosphate | 11.87% | 62.93 | | |
| d | Sodium Chloride crystalline | 76.20% | 404.11 | | |
| e | Sodium Bicarbonate | 8.26% | 43.82 | | |
| f | Silica | 0.46% | 2.43 | | |
| | TOTAL | 100.00% | 530.33 | | |

Example 4d was prepared by adding dibasic sodium phosphate anhydrous to ingredients used for Example 4c (Table 10). The phosphates level was reduced. This experiment showed the improved compatibility of calcium glycerophosphate compared to calcium chloride with dibasic sodium phosphate, as the dispersion produced was turbid but no particles in suspension and visible precipitates were observed.

TABLE 9

| Item | Ingredient name | % | mg/unit | Solubility in 30 ml of tap water | pH |
|---|---|---|---|---|---|
| a | Dibasic Sodium Phosphate Anhydrous | 2.57% | 13.78 | light cloudy suspension appearance | 7.23 |
| b | Monobasic Sodium Phosphate Anhydrous | 1.64% | 8.77 | | |
| c | Calcium Glycerophosphate | 11.74% | 62.93 | | |
| d | Sodium Chloride | 75.42% | 404.11 | | |
| e | Sodium Bicarbonate | 8.18% | 43.82 | | |
| f | Colloidal silicon dioxide | 0.45% | 2.43 | | |
| | TOTAL | 100.00% | 535.83 | | |

Example 4e is presented in Table 10, and it was prepared by reducing sodium bicarbonate ratio and increasing dibasic and monobasic sodium phosphates ratios (to their original ratios like Example 4a). The pH obtained was closer to 7.0. This formulation was considered promising as the phosphate and calcium contents are equivalent to the original Neutrasal formulation, and as the dispersion produced was turbid but no particles in suspension and no visible precipitate were observed.

TABLE 10

| Item | Ingredient name | % | mg/unit | Solubility in 30 ml of tap water | pH |
|---|---|---|---|---|---|
| a | Dibasic Sodium Phosphate Anhydrous powder | 4.98% | 26.78 | light cloudy suspension appearance | 6.95 |
| b | Monobasic Sodium Phosphate Anhydrous | 3.17% | 17.04 | | |
| c | Calcium Glycerophosphate | 11.64% | 62.65 | | |
| d | Sodium Chloride | 75.11% | 404.11 | | |
| e | Sodium Bicarbonate | 4.65% | 25.0 | | |
| f | Colloidal silicon dioxide | 0.45% | 2.43 | | |
| | TOTAL | 100.00% | 538.00 | | |

Based on ICP results from Example 4e, Example 4f was prepared by reducing the amounts of the two sodium phosphate salts and increasing calcium glycerophosphate ratio compared to Example 4f (Table 11). The objective was to obtain ratios of 22,000 ppm to 25,000 ppm calcium ions and 65,000 ppm to 70,000 ppm phosphate ions (as phosphate) per package.

The pH obtained was slightly higher than Example 4e at 7.23, but still with the 6.5-7.5 acceptable range. The dispersion produced was slightly turbid but less so than Example 4e.

TABLE 11

| Item | Ingredient name | % | mg/unit | Solubility in 30 ml of tap water | pH |
|---|---|---|---|---|---|
| a | Dibasic Sodium Phosphate Anhydrous | 1.31% | 7.05 | Very light cloudy suspension appearance | 7.23 |
| b | Monobasic Sodium Phosphate Anhydrous | 0.83% | 4.49 | | |
| c | Calcium Glycerophosphate | 13.37% | 71.92 | | |
| d | Sodium Chloride | 79.12% | 425.65 | | |
| e | Sodium Bicarbonate | 4.89% | 26.33 | | |
| f | Colloidal silicon dioxide | 0.48% | 2.56 | | |
| | TOTAL | 100.00% | 538.00 | | |

To summarize, the relatively high insolubility of the combination of dibasic sodium phosphate and calcium chloride was found to produce visible particles and precipitates. Surprisingly, the use of calcium glycerophosphate showed improved solubility in combination with dibasic sodium phosphate and led to a reconstituted turbid dispersion, but no visible particles or visible precipitates were observed.

Other advantages found by the foregoing examples of using calcium glycerophosphate are (1) increased pH which allows a reduction of sodium bicarbonate in the formulation; and (2) reduced lot-to-lot variability and handling issues versus calcium chloride. Indeed, calcium chloride dihydrate is extremely hygroscopic. Water content depends on storage conditions but also environmental conditions and duration in manufacturing. Humidity can cause calcium and phosphate molecules to react and form insoluble $Ca_3(PO_4)_2$ (tribasic calcium phosphate), thereby creating precipitation when the powder is mixed with water.

Example 4f is especially consistent with the objectives of a calcium ion content between about 22,000 ppm and about 25,000 ppm, a phosphate ion content between about 65,000 ppm and about 70,000 ppm and pH between about 6.5 and about 7.5. More particularly, it has a calculated calcium ion content of 22,923 ppm and a calculated phosphate ion content of 69,944 ppm (as phosphate). Both are calculated based on weight percentages of solid components in the powder.

In the foregoing embodiments and description, calcium lactate gluconate can be used in place of calcium glycerophosphate, except that the amounts of calcium lactate gluconate should be increased to about 2.1 fold of the amount of calcium glycerophosphate in order to obtain substantially the same calcium content in the powder or liquid.

With respect to the compositions described in the specification, it is intended that the specification also provides a description of methods of using any of those compositions in the described methods. With respect to the methods of manufacture described in the specification, it is intended that the specification also provides a description of the manufacture of any of the compositions described herein.

All of the references cited herein, including patents, patent applications, and publications, are hereby incorporated in their entireties by reference.

In general, terminology may be understood at least in part from usage in context. For example, terms, such as "and", "or", or "and/or," are used interchangeably unless the context dictates otherwise. In addition, the term "one or more" as used herein, depending at least in part upon context, may be used to describe any component in a singular sense or may be used to describe combinations of features, structures or characteristics in a plural sense. Similarly, terms, such as "a," "an," or "the," again, may be understood to convey a singular usage or to convey a plural usage, unless the context indicates otherwise. The phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

Ranges can be expressed as from "about" one particular value, and/or to "about" another particular value. When such a range is expressed, another aspect includes the one particular value and/or to exactly the other particular value. Similarly, when values are expressed as approximations, by use of the antecedent "about," it will be understood that the particular value forms another aspect and is disclosed by the present inventors. It is also understood that there are a number of values disclosed herein, and that each value is also herein disclosed as "about" that particular value in addition to the value itself. For example, if the value "10" is disclosed, then "about 10" is also disclosed.

While particular elements, embodiments and applications of the present invention have been shown and described, it will be understood, of course, that the invention is not limited thereto since modifications can be made by those skilled in the art without departing from the scope of the present disclosure, particularly in light of the foregoing teachings.

What we claim is:

1. A liquid composition supersaturated in calcium ions and phosphate ions, the liquid composition being a product of mixing a powder with water in a weight ratio of powder-to-water from about 0.005:1 to about 0.1:1, and wherein the powder comprises: (i) calcium glycerophosphate in an amount of from about 5% w/w to 25% w/w of the powder; (ii) dibasic sodium phosphate anhydrous in an amount of from about 0.5% w/w to about 10% w/w of the powder; (iii) monobasic sodium phosphate anhydrous in an amount of from about 0.3% w/w to about 6% w/w of the powder, and (iv) sodium chloride; and wherein the liquid composition has a pH of from about 6.5 to about 7.5 and is free of visible particles and precipitates.

2. The liquid composition of claim 1, wherein the dibasic sodium phosphate anhydrous is present in an amount of from about 0.5% w/w to about 4.5% w/w of the powder, and the monobasic sodium phosphate anhydrous is present in an amount of from about 0.3% w/w to about 2.5% w/w of the powder.

3. The liquid composition of claim 1, wherein the powder further comprises a pH buffering agent.

4. The liquid composition of claim 3, wherein the pH buffering agent is sodium bicarbonate present in an amount of from about 1% w/w to about 7.5% w/w of the powder.

5. The liquid composition of claim 1, wherein the powder further comprises silica.

6. The liquid composition of claim 1, wherein the powder comprises a concentration of calcium that is at least about 20,000 ppm, calculated based on weight percentages of solid components in the powder.

7. The liquid composition of claim 1, wherein the powder comprises a concentration of phosphate that is at least about 60,000 ppm, calculated based on weight percentages of solid components in the powder.

8. The liquid composition of claim 1, wherein the powder further comprises one or more of a fluoride salt, an analgesic, an antihistamine, a corticosteroid, an anti-microbial agent, an anti-fungal agent, a flavoring or a preservative.

9. A method for treating an oral injury, an oral inflammation, an oral pain, xerostomia, chronic hyposalivation or complications therefrom in a subject in need of such treatment, the method comprising:
   (a) admitting the liquid composition supersaturated in calcium ions and phosphate ions according to claim 1 into the oral cavity of the subject;
   (b) moving the composition within the oral cavity;
   (c) expelling the composition from the oral cavity of the subject.

10. The method of claim 9, wherein the subject is in need of treatment for xerostomia or chronic hyposalivation.

* * * * *